US006242478B1

(12) United States Patent
Welker et al.

(10) Patent No.: US 6,242,478 B1
(45) Date of Patent: Jun. 5, 2001

(54) FIVE MEMBER RING SULFENATE ESTERS AND THIOSULFINATE ESTERS (75) Inventors: Mark E. Welker; Suzy V. Torti; Frank M. Torti; Alan J. Townsend; Eva Pietsch, all of Winston-Salem, NC (US); Allison L. Hurley, Atlanta, GA (US)

(73) Assignee: Wake Forest University, Winston-Salem, NC (US)

( * ) Notice: Subject to any disclaimer, the term of this patent is extended or adjusted under 35 U.S.C. 154(b) by 0 days.

(21) Appl. No.: 09/459,261

(22) Filed: Dec. 10, 1999

(51) Int. Cl.[7] ................... A61K 31/385; A61K 31/39; C07D 339/04; C07D 327/04
(52) U.S. Cl. ..................... 514/439; 514/440; 549/35; 549/39; 549/40
(58) Field of Search .................. 549/35, 39, 40; 514/439, 440

(56) References Cited

PUBLICATIONS

Thoumazeau et al, Heterocycles, vol. 19, No. 12, pp. 2247–2250, 1982.*
Hurley et al, Organomettallics, vol. 17, No. 13, pp. 2832–2838, Jun. 1998.*
Raseta et al, Organometallics, vol. 10, No. 8, pp. 2936–2945, 1991.*
Buadin et al., Properties of some derivatives of 3,3–disubstituted propa–1,2–dienesulfinic acids [1], Bull. Soc. Chim. Fr. 132:79–85, 1995.
Bondarenko and Saginova, "Synthesis and properties of sultines, cyclic esters of sulfinic acids," Russian Chem. Reviews 65(2):147–66, 1996.
Braverman and Reisman, "Electrophilic Fragmentation–Cyclization of Various Allenic Esters," Tetrahedron Letters 20:1753–56, 1977.
Gupta et al., "Pharmacokinetics and Pharmacodynamics of Oltipraz as a Chemopreventive Agent", Clin. Cancer Research, 1:1133–38, 1995.
Hall and Smith, "Photolysis of Unsaturated Cyclic Sulphones," Tetrahedron Letters, 41:3633–36, 1974.
Hurley et al., "Reactions of Transition–Metal n1–Propargyl and n1–Alenyl Complexes with Sulfur Dioxide and Transition–Metal–Carbon Bond Cleaving Reactions of the Cycloadducts Which Yield Cyclic Sulfenate Esters," Organometallics, 17:2832–38, 1998.
King et al., "Thermolysis of thiete 1,1–dioxide and related species," Canadian J. Chem., 48:3704–15, 1970.
Kowalewski and Margaretha, "5–Isopropyliden–1,2–oxathiole 2–Oxide by Photoisomerization of 2,2–Dimethyl–3(2H)–thiophenone 1–Oxide," Angew. Chem. Int. Ed. Engl. 27(10):1374–5, 1988.
Prochaska et al., "Oltipraz, An Inhibitor of Human Immunodeficiency virus type 1 Replication," Proc. Natl. Acad. Sci. USA 90:3953–57, 1993.

Raseta et al., "Cycloaddition reactions of transition–metal 2–alkynyl complexes with a disulfur monoxide source, Transition–metal–mediated syntheses of five–membered–ring thiosulfinate esters," Organometallics, 10:2936–45, 1991.
Raseta, et al., "Transition Metal Mediated Thiosulfinate Ester Synthesis," J. Am. Chem. Soc., 111:8268–70, 1989.
Rice et al., "Inhibition of Multiple Phases of Human Immunodeficiency Virus Type 1 Replication by a Dithiane Compound That Attacks the Conserved Zinc Fingers of Retroviral Nucleocapsid Proteins," Antimicrobial Agents and Chemotherapy, 41(2):419–26, 1997.
Rice et al., "Inhibition of HIV–1 Infectivity by Zinc–Ejecting Aromatic C–nitroso Compounds," Nature 361:473–75, 1993.
Rice et al., "Inhibitors of HIV Nucleocapsid Protein Zinc Fingers as Candidates for the Treatment of AIDS," Science, 270:1194–97, 1995.
Talalay, "Mechanisms of Induction of Enzymes that Protect Against Carcinogenesis," Adv. Enz. Reg. 28:237–50, 1988.
Thoumazeau et al., "Sulfur Dioxide Insertion into g–Functional Vinylic Grignard Reagents, A Facile Synthesis of a,b–Unsaturated g–Sultines and g–Sultones," Heterocycles 19(12):2247–50, 1982.
Torosyan et al., "Preparation and reactions of 2–oxo–4–chloro–5,5–dimethyl—)3–1,2–oxathiole," Chem. Abstr. 106:678, No. 138299t, 1987.
Tummino et al., "The In Vitro Ejection of Zinc from Human Immunodeficiency Virus (HIV) Type 1 Nucleocapsid Protein by Disulfide Benzamides with Cellular Anti–HIV Activity," Proc. Nat. Acad. Sci. USA 93:969–73, 1996.
Urove and Welker, "Synthesis of a stable disulfur monoxide precursor and trapping of disulfur monoxide with transition metal complexes," Organometallics, 7:1013–14, 1988.
Wattenberg, An Overview of Chemoprevention: Current Status and Future Prospects, Proc. Soc. Exp. Biol. Med., 216:133–41, 1997.
Welker, "3 + 2 Cycloaddition reactions of transition–metal 2–alkynyl and n1–allyl complexes and their utilization in five–membered–ring compound syntheses," Chem. Rev., 92:97–112, 1992.

* cited by examiner

Primary Examiner—Bernard Dentz
(74) Attorney, Agent, or Firm—Timothy S. Corder; Vinson & Elkins LLP (57) ABSTRACT Disclosed are novel sulfenate esters and thiosulfinate esters that induce the expression of metabolic enzymes, particularly Phase II enzymes such as glutathione-s-transferase, DT-diaphorase and Ferritin H when administered to a subject. Also disclosed, such compounds are effective to displace a zinc ion from retroviral zinc finger nucleocapsid proteins effective to inhibit HIV replication. The present invention is further directed to novel methods of making these compounds, and any compounds produced by the process of making these novel compounds.

58 Claims, 2 Drawing Sheets

FIVE MEMBER RING SULFENATE ESTERS AND THIOSULFINATE ESTERS

The government may have an interest in this patent pursuant to research finds that were supplied in the form of a grant from the National Institutes of Health grant # R15GM51021.

FIELD OF THE INVENTION

The invention relates generally to novel sulfenate esters and thiosulfinate esters containing five membered rings, and to methods of making these compounds. The invention also relates to the field of therapeutic compositions for use as anti-cancer chemotherapeutic or chemoprotective agents, and as anti-HIV agents.

BACKGROUND OF THE INVENTION

Various types of cancers occur throughout the body, and affect large numbers of people. It is postulated that many of these cancers are caused by foreign substances, also referred to as xenobiotics. One method of limiting the carcinogenic effect of various xenobiotics is by promoting steps or increasing levels of substances in the metabolic pathway that allow carcinogens to be metabolized into neutral forms that are easily excreted from the body.

A simplified description of how xenobiotics, compounds foreign to the body, are metabolized is that procarcinogens are metabolized by Phase I enzymes to either (i) electrophilic metabolites, which may cause DNA damage leading to DNA repair mechanisms or to cancer, or to (ii) nonelectrophilic metabolites that are further metabolized by Phase II enzymes to produce detoxification products. Several steps in this pathway potentially neutralize xenobiotics, and therefore could be considered as logical targets for chemoprevention of cancer. For example, the induction or inhibition of phase I enzymes might promote neutralizing metabolic steps, as could the induction of phase II enzymes. Alternatively, the promotion of DNA repair is a potentially promising means of preventing the carcinogenic effect of xenobiotics that are metabolized through Phase I enzymes to produce electrophilic metabolites which damage nucleic acid structures.

The prevention of the development of cancer by administering drugs prophylactically has been termed chemoprevention. Chemoprevention is an emerging concept that envisages the active prevention of malignant processes. Chemoprevention involves the "use of specific natural or synthetic substances with the objective of reversing, suppressing or preventing carcinogenic progression . . . " (Singh and Lippman, 1998). A number of such chemopreventive agents are currently in development for undergoing clinical trials.

Chemopreventive agents can be conceptually classified as "blocking" or "suppressive" agents. Blocking agents prevent cancer-producing compounds from reaching or reacting with their critical target sites; suppressive agents prevent the evolution of the neoplastic process in cells already altered by carcinogens (see Singh and Lippman, 1998 for review). Thus, chemopreventive agents can be provided either to high risk groups or to the population at large.

Oltipraz can be considered to have both blocking and suppressive activities, and is being investigated for chemopreventive activity in a number of cancers, including those of the bladder, prostate, breast, skin, lung, colon, and liver (Wattenberg, 1997). A large scale clinical trial of the ability of oltipraz to prevent aflatoxin F1-related hepatocellular carcinoma is currently underway in the People's Republic of China. However, oltipraz has been associated with some toxicities, including photosensitivity/heat intolerance, GI effects, and neurologic toxicities (Dimitrov et al., 1992). Thus, the continued search for improved chemopreventive agents is clearly warranted.

Phase II enzymes are responsible for the detoxification of reactive electrophilic and nucleophilic metabolites. Phase II enzymes include NAD(PH):quinone oxidoreductase (facilitates metabolism of carcinogens through two electron reduction), glutathione S transferase (mediates deactivation of carcinogens through conjugation to reduced glutathione), manganese superoxide dismutase (reduces levels of superoxide anion) ferritin (reduces oxygen free radical formation by sequestering iron), and others (Talalay, 1989). Glutathione S-transferases (GST) are phase II enzymes that catalyze the reaction of glutathione, a tripeptide, with electrophiles such as epoxides, alkyl and aryl halides and $\alpha,\beta$-unsaturated ketones. Glutathione conjugation serves to deactivate electrophiles, therefore making them less toxic and carcinogenic and more easily excreted by the body.

In the reaction between glutathione and an electrophile, the first step involves the binding of glutathione (GSH) to the glutathione-S-transferase enzyme (GST). The enzyme is known to lower the pKa of the thiol from 9.0 to ~6.5. The thiolate ion of glutathione then reacts with electrophiles to produce the less toxic glutathione conjugates.

Several sulfur-containing compounds are known to elevate levels of GST in rats and mice. These include allicin (Talalay, et al.), a natural product found in garlic, and Oltipraz 10, which is undergoing clinical trials at the time of the present disclosure.

Oltipraz and its derivatives (1,2-dithiole-3-thiones) are particularly attractive because of two important characteristics. First, 1,2-dithiole-3-thiones are monofunctional inducers. They only induce phase II enzymes and not phase I enzymes. Induction of phase I enzymes could enhance the production of activated carcinogens, therefore complicating any increased activity of phase II enzymes. Secondly, 1,2-dithiole-3-thiones can induce higher levels of GSTs in several organs, providing possible protection against several types of cancer.

10

Because of this selective usefulness of sulfur-containing compounds that display an ability to induce high levels of GST in particular, industry is constantly seeking additional forms of such compounds, as well as reliable methods for their synthesis. As a result, several syntheses have been reported for unsaturated five-membered cyclic sulfenate esters or γ-sultines (Bondarenko, et al.); however, none of the reported syntheses to date are very general. In 1970, King and co-workers reported that thermolysis of thiete 1,1-dioxide and 2-phenylthiete 1,1-dioxide produced unsaturated sultines (King et al.) Thermolysis of other substituted thiete 1,1-dioxides resulted in sulfur dioxide extrusion to yield various alkenes.

Braverman and co-workers have studied the electrophilic fragmentation and cyclization of allenic sulfones to unsat- urated γ-sultines (Braverman and Duar). Allenyl sulfone when reacted with bromine produced a bromonium ion intermediate which cyclized to produce sultine. This reaction is unfavorably limited, however, because only bromine substituted sultines can be synthesized.

Another synthesis of unsaturated sultines reported by Duboudin and co-workers required Grignard reagents formed from propargyl alcohols (Thomazeau et al.). The resulting Grignards reacted with sulfur dioxide by insertion into the carbon-metal bond. The sultines were obtained, however, in poor to moderate yields.

Accordingly, novel compounds that can induce GST and other enzymes of the Phase II response, and a method of reliably synthesizing such compounds in various forms while resulting in useful levels of the desired product is still sought.

The tendency of HIV-1 to mutate to viral strains that are resistant to existing therapeutic regimens is now well documented (Cohen, 1997). This resistance has fueled the search for antiviral drug targets that are conserved through mutations. The zinc finger containing nucleocapsid proteins of retroviruses would appear to be such a therapeutic target since they are conserved through mutations, are involved in early and late phases of the viral replication cycle, and are chemically reactive toward soft electrophilic reagents that can be prepared via rational synthetic structure-activity modification schemes (Rice and Turpin, 1996). The structure of the HIV-1 nucleocapsid protein (NCp7) was determined in the early 1990's (South et al., 1990; Chance, et al., 1992; Summers et al., 1992) and found to have the Cys-Xaa$_2$-Cys-Xaa$_4$-His-Xaa$_4$-Cys zinc coordination sphere sequence with the short tether links that are now sometimes referred to as a "zinc knuckle". At that same time Rice and co-workers first postulated that the Cys residues of zinc fingers could be chemically modified by electrophilic attack. They first demonstrated the viability of this chemical postulate using 3-nitrosobenzamide (NOBA) (Rice et al., 1993). While NOBA reacted with the zinc fingers of NCp7 causing zinc ejection, it was reduced to an aromatic hydroxylamine. This class of compounds is known to be quite mutagenic (Nohmi, et al., 1984) so the Rice group initiated a search for other soft electrophilic functional groups which would react with the sulfur rich zinc finger domain.

The disulfide functional group has the desired chemical reactivity and the Rice group had access to a host of 2,2'-dithiobisbenzamides (DIBAs) (3) (submitted by Parke-Davis Pharmaceutical) via NCI's Developmental Therapeutics Program (Rice et al., 1995; Rice et al., 1996; Tummino et al., 1996). These compounds were used by Rice et al. (1995 and 1996) and the Parke-Davis group (Tummino et al., 1996) to definitively correlate ability to eject zinc from the NCp7 protein with the ability of the compounds to exert anti-HIV-1 activity.

R' = substituted benzamides

Unfortunately, reaction of these acyclic disulfides (RSSR) (3) with intracellular reducing agents/nucleophiles such as reduced glutathione produced two thiols (RSH) which no longer react with the zinc fingers. This observation lead to a search for cyclic disulfides and analogs thereof, particularly for a molecule in which the 2 thiols could not dissociate from one another, thereby effectively rendering redox return to the disulfide impossible. Lamar Field's group had deposited a number of 1,2-dithiolanes (4) and 1,2-dithianes (5) in NCI's chemical repository and the Rice group screened a number of these (Rice et al., 1997).

Two of the six 1,2-dithiolanes (6, 7) and two (8, 9) of the 13 1,2-dithianes screened were active against HIV-1$_{RF}$ replication in CEM-SS cells in the XTT-based cytoprotection assay, were active against replication of monocytotropic HIV-1$_{ADA}$ in fresh human monocyte/macrophage cultures and promoted ejection of zinc from the NCp7 protein. Both the XTT and monocyte/macrophage assays were used because infection of monocyte/macrophage cultures is thought to resemble infection of the nonproliferating pool of cells in vivo, while the parameters for the CEM-SS cells (XTT assay) are thought to reflect more closely the parameters for highly proliferating cells such as bone marrow and intestinal cells. The CEM-SS cell (XTT) assay is a more sensitive indicator of toxicity and all compounds disclosed herein have been screened in this assay.

TABLE 1

Anti-HIV-1 and Zinc Ejection Screening of 6, 7, 8, 9

| # | NSC # | XTT Assay (μM) | | Monocyte/ Macrophage Assay (μM) | | TSQ NCp7 Assay |
|---|---|---|---|---|---|---|
| | | EC$_{50}$ | IC$_{50}$ | EC$_{50}$ | IC$_{50}$ | |
| 6 | 661127 | 34 | 200 | N/A* | N/A* | |
| 7 | 661126 | 9.8 | 30 | 21 | >100 | 18 |
| 8 | 624151 | 6.6 | 184 | 8.0 | >100 | 17 |
| 9 | 624152 | 13 | 135 | 9.1 | >100 | 20 |

N/A* No material was available for further testing.

The most active, least toxic compound, NSC 624151 (8), was then screened for of antiviral action against a variety of strains of HIV-1 and found to be active (3–69 μM depending on strain) against all tested strains. NSC 624151 (8) was found to promote zinc ejection from the NCp7 protein but have no other observable effect on enzymatic activities of the viral replication cycle.

The antiviral mechanism of action is postulated to be electrophilic attack of the oxidized organosulfur compounds on the nucleophilic/reducing cys residues present in the zinc fingers. Structurally related organosulfur compounds are known to be soft electrophiles and susceptible to nucleophilic attack by soft nucleophiles such as thiols and thiolate anions (Talalay et al., 1988). These types of compounds are also substrates for glutathione S-transferases, a family of enzymes involved in detoxification of electrophiles and chemoprevention of cancer (Wilce and Parker, 1994); Coles and Ketterer, 1990; Armstrong, 1991), and as discussed in the preceding paragraphs. Oltipraz (10) has also been shown to prevent HIV-1 replication (Prochaska et al., 1993). Since reduced glutathione is a potential competing intracellular nucleophile/reducing agent present in high concentrations in all cells, NSC 624151 (8) was also screened in the XTT cytoprotection assay in the presence of a two fold excess of glutathione (GSH). Antiviral activity was retained but the $EC_{50}$ did increase by a factor of almost 10 from 6.6 μM to 64.2 μM. Toxicity was also decreased with GSH treatment with $IC_{50}$ going from 184 μM to >200 μM. The competing nucleophile/reducing agent glutathione does reduce but does not eliminate the anti-HIV activity of these compounds.

After discovery that the cyclic dithianes and dithiolanes still maintain anti-HIV-1 activity even in the presence of reduced glutathione, the Rice group began to tackle the critical question of zinc finger specificity. Can compounds be produced which will selectively target retroviral nucleocapsid protein zinc fingers without affecting other cellular zinc fingers? This group has now shown that dithiane (8) does not affect poly (ADP-ribose) polymerase (PARP) activity or alter specific binding of the zinc finger containing transcription factors Sp1 and GATA-1 to their DNA targets (Huang et al., 1998). Lastly, they also examined the effect of NSC 624151 (8) on in vitro transcription using HeLa nuclear extract. A CMV promoter was used to drive the transcription of a duck HBV sequence and 8 did not significantly alter this transcriptional process either.

Maynard and Covell have came out with a density functional theory (DFT) analysis, in combination with protein-ligand docking methods, for predicting reactivity of NCp7 with electrophilic reagents (Maynard et al., 1998). They found that the molecular property of these soft electrophiles that correlated most strongly with their reactivity toward NCp7 and zinc ejecting ability was the ratio of electronegativity to hardness ($\chi^2/\eta$). This quantity is related to the capacity of an electrophile to promote a soft, covalent bond forming reaction. Calculation of $\chi^2/\eta$ for a variety of zinc ejectors was presented along with protein-ligand docking analysis.

From the DFT calculations, they observed a linear correlation between NCp7 reaction rates and the ligand's capacity to promote a soft, covalent reaction, $\chi^2/\eta$. The most reactive DIBA compounds (3, R'=C(O)NH-phenyl-$SO_2NH_2$ and R'=C(O)NH-phenyl-$SO_2NHC(O)CH_3$ had $\chi^2/\eta$ values of 0.2935 and 0.3098 respectively. The next most reactive compound, dithiane, (9) had a $\chi^2/\eta$ value of 0.2260. Compounds with $\chi^2/\eta$ values of less than 0.2 exhibited relatively poor zinc ejecting ability.

The NMR structure of NCp7 was then used as a fixed model for ligand docking analysis. Zinc finger 1 and zinc finger 2 docks were examined and Fukui functions of the Cys thiolates ($S^{15}$, $S^{18}$, and $S^{28}$ in finger 1 and $S^{39}$ and $S^{49}$ in finger 2) were calculated and their proximity to the ligand electrophilic sites in the best scoring docks were calculated. Zinc finger 2 is known to be 7 fold more reactive (Rice et al., 1995; Rice et al., 1996; Tummino et al., 1996; Huang et al., 1998) than zinc finger 1 with the DIBA compounds (3) and this observation correlated well with calculated binding proximities. Frontier molecular orbital $Cys^{49}$ HOMO to electrophile LUMOs were then calculated and dithiane (9) showed high orbital overlap consistent with its chemical reactivity. This ligand docking analysis predicted a saddle shaped docking domain of each zinc finger and two nearly equivalent binding sites (designated α and β) for most small molecules inside the saddle.

Rice, Turpin and co-workers have reported new compounds capable of binding to both the α and β sites of zinc finger 2 and they included the Covell/Maynard calculations of their most likely binding conformations (Rice et al., 1999). In this study, they abandoned the disulfide linkage in 3 in favor of a thioester linkage (11). As mentioned earlier, acyclic disulfides can be deactivated in this chemistry by reduction to the thiolates. The monomeric thiolates can then simply diffuse away from one another rather than recombine after reoxidation. Cyclic compounds such as 9 do not suffer from this functional group disadvantage.

Extensive synthetic work reported in this paper resulted in the identification of pyridinoalkanoylthiolesters (PATEs) (11) as compounds that could span both a and β docking sites and provide a soft electrophilic thioester group in close proximity to $Cys^{49}$. These compounds had antiviral $EC_{50}$'s in the XTT cytoprotection assay of 5–6 μM and exhibited zinc finger reactivity, as measured by the Trp37 fluorescence decrease assay of 3–4 relative fluorescence units/min over 30 minutes.

11

The inventor is also familiar with work in which 32 different sulfur heterocycles and sulfur containing transition metal complexes were screened in the XTT cytoprotection assay and zinc ejection assay described herein above. Of the 18 metal complexes screened, only 1 (31) had antiviral activity and it did not have an $EC_{50}$. Cytoprotection of 39% was observed at 100 μM and its $IC_{50}$ was 154.5 μM.

31

$$OC_{\prime\prime\prime\prime\prime}\overset{Cp}{\underset{Bu_3P}{|}}\overset{}{\underset{}{Fe}}\overset{}{\underset{SO_2CH_3}{}}$$

It would be advantageous, therefore to provide specific antiviral agents, capable of ejecting zinc from viral zinc finger configurations, in order to effectively address the mutational defense mechanisms of HIV. The present disclosure is believed to address this deficiency in the art, by providing novel compounds with anti-HIV activity and that are also useful in the prevention of certain cancers.

SUMMARY

The present invention provides novel sulfenate esters and five membered ring thiosulfinate esters that are shown herein to have useful biological activities. The disclosed compounds may be used in therapeutic formulations to be administered to human or animal subjects who have been exposed to, or may be exposed to certain cancer causing xenobiotics, or to humans or animals subject to developing certain types of cancer, or to humans infected with HIV. The disclosed compounds may also be administered with the goal of preventing cancer in normal or healthy subjects.

The present disclosure includes compositions that contain pharmaceutically active agents that are effective in the treatment or prevention of various neoplastic diseases that include, but are not limited to cancer of the bladder, prostate, breast, skin, lung, colon, liver, or pancreas, including invasive and non-invasive adenocarcinomas, and other cancers that occur in a tissue that expresses GST's or related metabolic enzymes, or in the treatment or management of a retroviral infection such as an infection with the human immunodeficiency virus (HIV).

An effective dose would include daily dosages of from about 1, 2, 3, 5 to about 125, 300, 500, 600, or even about 1000 mg/kg/day of the active agents. Agents may be administered in a single daily dose, or split into 2, 3 or more doses to be taken throughout the day. Preferred regimens may include taking the compositions daily for a week or more, for several weeks, and even daily or weekly for a period of about 12 weeks or more. If used in chemoprevention, long term administration (years) is envisioned. The dosage and administration will be determined by a practitioner and will be based on the condition and need of the individual patient, of course.

The active agents described herein may also be administered in combination with other active agents, particularly oncology agents, or anti-viral agents including, but not limited to anti-inflammatory drugs such as ibuprofen, aspirin, acetaminophen, anti cancer drugs such as various retinoids, including but not limited to 13-cis-retinoic acid, retinol, or 4-hydroxyphenylretinamide, other possible anti-cancer agents such as beta-carotene, piroxicam, oltipraz, difluoromethylomithine, glycyrrhetinic acid, N-acetylcysteine, sodium molybdate, alpha-angelicalactone, alpha-tocopherol, coumarin, ellagic acid, flavone, indole-3-carbinol, d-limonene, phenethylisothiocyanate, mechlorethamine, chlorambucil, cyclophosphamide, melphalan, ifosfamide, methotrexate, 6-mercaptopurine, 5-fluorouracil, cytarabine, gemcitabine, vinblastine, vincristine, vinorelbine, paclitaxel, docetaxel, etoposide, irinotecan, topotecan, doxorubicin, bleomycin, mitomycin, carmustine, lomustine, cisplatin, carboplatin, interferons (interferon A), asparaginase, zidovudine, didanosine, zalcitabine, stavudine, lamivudine, nevirapine, delavirdine, saquinavir, indinavir, ritonavir, and nelfinavir.

The present invention may be described, therefore in certain preferred embodiments as a composition comprising a five membered ring thiosulfinate ester, or a five-membered ring sulfenate ester, wherein the five membered ring has structure (I)

(I)

wherein, when X is O or S;

$R_1$ is an alkyl, preferably with 1–6 carbon atoms and more preferably methyl, phenyl, substituted phenyl, cyclohexenyl, or substituted cyclohexenyl;

$R_2$ is methyl, phenyl or $CO_2R_3$, wherein $R_3$ is alkyl or phenyl; and when X is O and $R_1$ is phenyl, $R_2$ is not methyl. As used herein, chemical element abbreviations are given their art-accepted meanings. For example, O indicates Oxygen, S indicates Sulfur, and C indicates Carbon, Me indicates a methyl group, Et indicates an ethyl group, Pr indicates a propyl group, iPr indicates an isopropyl group, t-Bu indicates a tert-butyl group, etc. In contrast, X, Y, and R are indicative of variables.

In preferred embodiments, when $R_1$ is a substituted phenyl, the phenyl is substituted at the 4 position with a methoxy, t-butyl, alkyl ketone, sulfonamide, or trifluoromethyl group. Furthermore, when $R_1$ is a substituted cyclohexenyl, the cyclohexenyl is preferably substituted in the 2 position with a halogen, an alkyl, or a phenyl. In certain preferred embodiments, X is O, $R_1$ is (4-MeO)phenyl, (4-t-Bu)phenyl or cyclohexenyl and $R_2$ is methyl. In certain preferred embodiments, X is O, $R_1$ is phenyl, and $R_2$ is alkyl, and preferably $R_2$ is methyl, ethyl, propyl, or isopropyl.

In certain embodiments, when X is O, $R_1$ is phenyl, and $R_2$ is $CO_2R_3$, where $R_3$ is preferably methyl, ethyl, propyl or isopropyl. Alternatively, when X is O, $R_1$ is cyclohexenyl, and $R_2$ is alkyl, preferably methyl, or phenyl. Furthermore, in certain embodiments, when X is O, $R_1$ is (4-MeO)phenyl and $R_2$ is $CO_2R_3$, or when X is O, $R_1$ may be (4-trifluoromethyl)phenyl, 4-acylphenyl, 4-sulfonamidylphenyl, or a cyclohexenyl with a halogen, preferably chloride, fluoride, bromide or iodide substituted at the 2 position. In certain embodiments, when X is O, $R_1$ is a cyclohexenyl with an alkyl substitution at the 2 position, and preferably an alkyl comprising 1 to 4 carbon atoms, or $R_1$ is a cyclohexenyl with a phenyl substitution at the 2 position.

In certain preferred embodiments of the compositions described above, when X is S, $R_1$ is phenyl or an alkyl with 1–6 carbon atoms, preferably methyl, and $R_2$ is $CO_2R_3$, where $R_3$ is preferably methyl, ethyl, isopropyl, or propyl. In alternative embodiments, X is S, $R_1$ is (4-MeO)phenyl, (4-t-Bu)phenyl or cyclohexenyl, and $R_2$ is methyl. In still further preferred embodiments, X is S, $R_1$ is phenyl, and $R_2$ is alkyl, and preferably $R_2$ is methyl, ethyl, propyl, or isopropyl. In certain embodiments, X is S, $R_1$ is cyclohexenyl, and $R_2$ is alkyl, preferably methyl, or $R_2$ may be phenyl.

In further embodiments of the disclosed formulations, when X is S, and $R_1$ may be methyl, (4-trifluoromethyl) phenyl, 4-acylphenyl, 4-sulfonamidylphenyl, or alternatively, $R_1$ is (4-MeO)phenyl and $R_2$ is $CO_2R_3$.

In certain embodiments, X is S, and $R_1$ is a cyclohexenyl with a halogen substitution, preferably chloride, fluoride, bromide or iodide at the 2 position, or alternatively $R_1$ is a cyclohexenyl with an alkyl substitution at the 2 position, preferably an alkyl with 1 to 4 carbon atoms, or $R_1$ is a cyclohexenyl with a phenyl substitution at the 2 position.

In certain embodiments, a composition as described herein will have an additional element Y as shown in structure (II):

(II)

As can be seen, if the Y group is removed from structure II, the result is structure I. In certain preferred embodiments, Y is O, $R_1$ is phenyl and $R_2$ is methyl, phenyl or hydrogen. It is understood that any of the compositions described herein as derived from structure I or II may be contained in a pharmaceutically acceptable carrier, and preferably a pharmaceutical carrier, or pharmacological formulation prepared for oral administration.

The present invention may also be described, in certain preferred embodiments as a pharmaceutical composition comprising a five membered ring thiosulfinate ester, or a five-membered ring sulfenate ester, wherein the five membered ring has structure (II) in an amount effective to induce glutathione-S-transferase (GST), DT-diaphorase (NQO1), or Ferritin H expression when administered to a subject; and further wherein when X is O or S;

$R_1$ is an alkyl with 1–6 carbon atoms, preferably methyl, phenyl, substituted phenyl, cyclohexenyl, or substituted cyclohexenyl;

$R_2$ is methyl, phenyl or $CO_2R_3$, wherein $R_3$ is alkyl or phenyl; and Y is not present or Y is O. It will be clear to those of skill in the art in light of the disclosure, that when Y is not present, then structure (II) is equivalent to structure (I).

An embodiment of the disclosure may also be described as a composition including a unit dose effective to inhibit or decrease the incidence of cancer in a subject, such as an animal or human subject, and in certain cases, an amount effective to induce glutathione-S-transferase (GST), DT-diaphorase (NQO1), or Ferritin H or other phase II enzymes expression in a subject when the composition is administered to the subject periodically. In certain embodiments, a subject to receive this composition is a human or animal that has been exposed to, or is susceptible to being exposed to a carcenogenic xenobiotic agent. In certain embodiments, a subject to receive this composition is an unaffected (normal) human. In certain embodiments, the described compositions may also be used to inhibit replication of certain viruses, including retroviruses, and in particular HIV. As such, the present invention includes pharmaceutical compositions in an amount effective to inhibit HIV replication when the composition is administered to a subject, and in particular to a human HIV patient.

As described herein an effective amount is from about 1 to about 1000 mg per dose, or from about 5 to about 600 mg, or even from about 100 to about 500 mg. As a chemopreventive, for such dosages are preferably a single daily dose taken orally, and may be administered for days, weeks, or even years. For treatment of HIV, such doses may be administered periodically in order to achieve continued inhibition of viral replication. It is understood that these compositions may be used as adjunct therapy with any compatible chemotherapeutic agent in the treatment of HIV, or in prevention of cancer.

Any numerical values recited herein include all values from the lower value to the upper value in increments of one unit provided that there is a separation of at least two units between any lower value and any higher value. As an example, if it is stated that the concentration of a component or value of a process variable such as, for example, osmolality, temperature, pressure, time and the like, is, for example, from 1 to 90, preferably from 20 to 80, more preferably from 30 to 70, it is intended that values such as 15 to 85, 22 to 68, 43 to 51, 30 to 32 etc. are expressly enumerated in this specification. For values which are less than one, one unit is considered to be 0.0001, 0.001, 0.01 or 0.1 as appropriate. These are only examples of what is specifically intended and all possible combinations of numerical values between the lowest value and the highest value enumerated are to be considered to be expressly stated in this application in a similar manner.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DETAILED DESCRIPTION

The present invention provides novel and useful compositions that include unsaturated five member ring containing sulfenate esters and thiosulfinate esters. These compositions are shown herein to have at least one of the following useful biological activities, either as agents for the prevention or protection against certain cancers, especially activity as inducers of glutathione-S-transferase expression, NQO1 DT-diaphorase expression, Ferritin H expression, or expression of other enzymes of the Phase II response, an activity useful in the defense against cancer causing xenobiotic agents and cancer prevention, or activity as anti-HIV agents that eject the $Zn^{2+}$ ion from a zinc finger nucleocapsid protein in HIV. Specific examples of the sulfenate esters provided include the novel GST-inducers 4-methyl-5-(4-methoxy)phenyl-1,2-oxathiol-4-en-1-yl oxide and 4-methyl-5-cyclohexenyl-1,2-oxathiol-4-en-1-yl oxide.

Additionally, the present disclosure provides methods of manufacturing these and additional compounds that may be screened for their capacity to induce elevated levels of GST, NQO1 or Ferritin H, and other Phase II enzymes, and may prove useful as cancer chemoprotectants or cancer chemotherapeutics. In general, the novel process of synthesizing compounds disclosed herein includes the steps of making an alkynyl alcohol; converting the alkynyl alcohol to an alkynyl tosylate; forming an iron alkynyl complex from an alkynyl tosylate; performing transition-metal mediated [3+2] cycloaddition of the iron alkynyl complex with sulfur dioxide or disulfur monoxide to produce an iron sulfenate ester or thiosulfinate ester; and from this, producing useful sulfenate esters and thiosulfinate esters.

Pharmacological Compositions

The active compounds may be orally administered, for example, with an inert diluent or with an assimilable edible carrier, or they may be enclosed in hard or soft shell gelatin capsule, or they may be compressed into tablets, or they may be incorporated directly with the food of the diet. For oral therapeutic or prophylactic administration, the active compounds may be incorporated with excipients and used in the form of ingestible tablets, buccal tables, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of the unit. The amount of active compounds in such therapeutically useful compositions is such that a suitable dosage will be obtained.

The tablets, troches, pills, capsules and the like may also contain the following: a binder, as gum tragacanth, acacia, cornstarch, or gelatin; excipients, such as dicalcium phosphate; a disintegrating agent, such as corn starch, potato starch, alginic acid and the like; a lubricant, such as magnesium stearate; and a sweetening agent, such as sucrose, lactose or saccharin may be added or a flavoring agent, such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup of elixir may contain the active compounds sucrose as a sweetening agent methyl and propylparabens as preservatives, a dye and flavoring, such as cherry or orange flavor. Of course, any material used in preparing any dosage unit form should be pharmaceutically pure and substantially non-toxic in the amounts employed. In addition, the active compounds may be incorporated into sustained-release preparation and formulations.

The active compounds may also be administered parenterally or intraperitoneally. Solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the form must be sterile and must be fluid. It must be stable under the conditions of manufacture and storage and must be preserved against the contaminating action of microorganisms, such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE 1

Preparation of Sulfenate Esters

The following example describes in detail the preparation of two novel five member ring sulfenate esters, compounds 121 and 123, which have been designated by the inventor as compounds ALH-556 (121) and ALH-562 (123).

A. Synthesis of Alkynyl Alcohols 95 and 99–101

First, the appropriate alkynyl alcohols are synthesized. To produce the particular compositions disclosed herein, 1-Ethynylcyclohexene, for example, is deprotonated with butyl lithium and then condensed with paraformaldehyde (Brandsma and Verkruijsse). By this process, 3-Cyclohexenyl-2-propyn-1-ol was produced in 82% yield (Baudouy, et al.). This compound had been reported previously without complete spectroscopic data (Baudouy). 1-Ethynylcyclohexene (3.00 g, 28.6 mmol) was dissolved in diethyl ether (125 mL) and cooled to −78° C. 2.5 M n-butyllithium in hexane (12.4 mL, 31.1 mmol) was added dropwise. The solution was allowed to stir at −78° C. for 1.5 h and then paraformaldehyde (1.70 g, 56.5 mmol) was added. The reaction mixture was allowed to warm to 25° C. overnight. The mixture was poured into sat. $NH_4Cl$ solution (125 mL) and then extracted with diethyl ether (3×50 mL). The ether extracts were dried with $MgSO_4$ and the solvent was removed under reduced pressure. The crude product was purified by column chromatography on silica gel using 1:1 diethyl ether/pentane to yield a light yellow oil (3.17g, 23.3 mmol, 82.4%). $^1H$ NMR ($CDCl_3$): 6.09 (m, 1 H), 4.35 (s, 2 H), 2.07 (m, 4 H), 1.62–1.57 (m, 5 H). EI HRMS (m/e) called for (M+)($C_9H_{12}O$) 136.0888, found 136.0894.

General Procedure for the Synthesis of Substituted Phenyl Propargyl Alcohols

Other useful alkynyl alcohols may be synthesized by the coupling of an appropriate aryl iodide with propargyl alcohol using Pd(PPh$_3$)$_2$Cl$_2$ and copper (I) iodide (Yang and Burton; Kondo, et al.). For example, 4-Iodoanisole was converted to 3-(4-Methoxy)-phenyl-2-propyn-1-ol in 98% yield (Wadsworth et al.). Alternatively, 3-(4-tert-butyl)-phenyl-2propyn-1-ol was isolated in 85% yield from the coupling of 1-tert-butyl-4-iodobenzene with propargyl alcohol. By way of further example, the coupling reaction of 1-Iodo-nitrobenzene and propargyl alcohol produced 3-(4-Nitro)-phenyl-2-propyn-1-ol in 89% yield (Harris, et al.).

The appropriate iodobenzene was dissolved in triethylamine (10–50 mL) and propargyl alcohol was added. The reaction mixture was thoroughly deoxygenated using nitrogen. Pd(PPh$_3$)$_2$Cl$_2$ (0–01 mol %) and CuI (0.02 mol %) were added and the resulting solution was allowed to stir for 2 h at 25° C. H$_2$O (20–40 mL) and ethyl acetate (20–40 mL) were added. The aqueous layer was extracted with ethyl acetate (2×20 mL). The organic extracts were combined and dried with MgSO$_4$. The solvent was removed under reduced pressure. The crude products were purified by recrystallization or column chromatography on silica gel.

3-(4-Methoxy)-phenyl-2-propyn-1-ol.

4-Iodoanisole (5.00 g, 21.4 mmol), propargyl alcohol (1.25 mL, 21.4 mmol), Pd(PPh$_3$)$_2$Cl$_2$ (0.150 g, 0.214 mmol) and CuI (0.082 g, 0.428 mmol) were reacted using the above procedure to yield a crude product which was purified by column chromatography using silica gel with 100% diethyl ether. The resulting off-white solid (3.40 g, 21.0 mmol, 98.3 %) proved identical by spectroscopic comparison to previously reported material (Wadsworth, et al.).

3-(4-tert-butyl)-phenyl-2-propyn-1-ol.

1-tert-Butyl-4-iodobenzene (1.00 g, 3.84 mmol), propargyl alcohol (0.223 mL, 3.84 mmol), Pd(PPh$_3$)$_2$Cl$_2$ (0.027 g, 0.038 mmol) and CuI (0.0 15 g, 0.077 mmol) were reacted using the above procedure to yield a crude product which was purified by column chromatography using silica gel with 100% diethyl ether. The resulting product was a light yellow solid (0.615 g, 3.27 mmol, 85.1%), m.p. 94–95° C. $^1$H NMR (CDCl$_3$): 7.33 (m, 4 H), 4.47 (s, 2 H), 1.90 (br s, 1 H), 1.29 (s, 9 H). Anal. Calcd for C$_{13}$H$_{16}$O: C, 82.94; H, 8.57. Found: C, 82.18; H, 8.54. E1HRMS (m/e) calcd for M$^+$ (Cl$_{13}$H$_{16}$O), 188.1201, found 188.1203.

3-(4-Nitro)-phenyl-2-propyn-1-ol.

1-Iodo-4-nitrobenzene (5.00 g, 20.1 mmol), propargyl alcohol (1.17 ml, 20.1 mmol), Pd(PPh$_3$)$_2$Cl$_2$ (0.140 g, 0.200 mmol), and CuI (0.076 g, 0.400 mmol) were reacted using the above procedure to yield a crude product which was purified by recrystallization from ethyl acetate and pentane. The tan solid (3.18 g, 17.9 mmol, 89.3%) proved identical by spectroscopic comparison to previously reported material (Harris, et al.)

B. Preparation of Alkynyl Tosylates

The alkynyl alcohols produced from step one, may then be converted into alkynyl tosylates. Propargyl alcohol was dissolved in diethyl ether (100 mL) and p-toluene sulfonyl chloride (0.95 equiv.) was added. The solution was cooled to −15° C. and powdered potassium hydroxide (5.0 equiv.) was added 1 equivalent at a time over 30–45 min. The reaction mixture was then allowed to stir at −15° C. for 90 min. Ice water (100 mL) was then added and the mixture was extracted with diethyl ether (3×50 mL). The solution was dried with MgSO$_4$ and the solvent was removed under reduced pressure. The product was then triturated with petroleum ether (15 mL), cooled to −78° C., and the solvent was decanted. The remaining product was dried under vacuum.

Tosylates 1-tosyl-3-cyclohexenyl-2propyne, 1-Tosyl-3-(4-methoxy)phenyl-2-propyne, and 1-Tosyl-3-(4-tert-butyl) phenyl-2-propyne were prepared in 92%, 84% and 68% yield respectively. Tosylate 1-Tosyl-3-(4-nitro)phenyl-2-propyne was prepared in 59% yield from 3-(4-Nitro)-phenyl-2-propyn-1-ol at 25° C. rather than the standard temperature of −10° C.

1-Tosyl-3-cyclohexenyl-2-propyne.

3-cyclohexenyl-2-propyn-1-ol (95)(3.04 g, 22.3 mmol), p-toluene sulfonyl chloride (4.04 g, 21.2 mmol) and potassium hydroxide (6.26 g, 112 mmol) were reacted using the above procedure to yield the product (5.66 g, 19.5 mmol, 91.8%) as a light yellow oil. $^1$H NMR (CDCl$_3$): 7.79 (d, J=8.1 Hz, 2 H), 7.31 (d, J=8.1 Hz, 2 H), 5.97 (m, 1 H), 4.81 (s, 2 H), 2.42 (s, 3 H), 2.02 (m, 2 H), 1.92 (m, 2 H), 1.53 (m, 4 H). FAB LRMS (m/e): calcd. for (MH$^+$)$^{(C}$$_{16}$H$_{19}$O$_3$S): 29 1, found 29 1.

1-Tosyl-3-(4-methoxy)phenyl-2-propyne.

3-(4-methoxy)phenyl-2-propyn-1-ol (3.56 g, 22.0 mmol), p-toluene sulfonyl chloride (3.97 g, 20.9 mmol), and potassium hydroxide (6.16 g, 110 mmol) were reacted using the above procedure to yield the product (5.50 g, 17.4 mmol, 83.7%) as a white solid: m.p. 44–45° C. $^1$H NMR (CDCl$_3$): 7.83 (d, J=8.2 Hz, 2 H), 7.29 (d, J=8.2 Hz, 2 H), 7.18 (d, J=8.7 Hz, 2 H), 6.78 (d, J=8.7 Hz, 2 H), 4.91 (s, 2 H), 3.78 (s, 3 H), 2.38 (s, 3H). FAB LRMS (m/e): calcd. for (MH+) (Cl$_{17}$H$_{17}$O$_4$S): 317, found 317.

1-Tosyl-3-(4-tert-butyl)phenyl-2-propyne.

3-(4-tert-butyl)phenyl-2-propyn-1-ol (0.550 g, 2.92 mmol), p-toluene sulfonyl chloride (0.529 g, 2.77 mmol) and potassium hydroxide (0.819 g, 14.6 mmol) were reacted using the above procedure to yield the product (0.649 g, 1.90 mmol, 68.4%) as a white solid: m.p. 83–84° C. $^1$H NMR (CDCl$_3$): 7.83 (d, J=8.1 Hz, 2 H), 7.31–7.26 (m, 4 H), 7.16 (d, J=7.9 Hz, 2 H), 4.93 (s, 2 H), 2.37 (s, 3 H), 1.28 (s, 9 H). Anal. Calcd for C$_{20}$H$_{22}$O$_3$S: C, 70.15; H, 6.48. Found: C, 70.09; H, 6.59.

1-Tosyl-3-(4-nitro)phenyl-2-propyne.

3-(4-nitro)phenyl-2-propyn- 1-ol (3.18 g, 18.0 mmol), p-toluene sulfonyl chloride (3.25 g, 17.1 mmol), and potassium hydroxide (5.04 g, 89.8 mmol) were reacted using the above procedure except that the reaction mixture was allowed to stir overnight at 25° C. to yield a yellow solid (3.32 g, 10.0 mmol, 58.8%): m.p. 103–104° C. $^1$H NMR (CDCl$_3$): 8.14 (d, J=8.5 Hz, 2 H), 7.84 (d, J=8.0 Hz, 2 H), 7.40 (d, J=8.5 Hz, 2 H), 7.33 (d, J=8.0 Hz, 2 H), 4.94 (s, 2 H), 2.40 (s, 3 H). Anal. Calcd. for C$_{16}$H$_{13}$NO$_5$S: C, 57.99; H, 3.95. Found: C, 57.7 1; H, 4.06.

C. Synthesis of Iron Alkynyl Complexes

The alkynyl tosylates obtained from step two are then reacted with the cyclopentadienyl iron dicarbonyl anion to yield desired iron alkynyl complexes.

The iron anion was generated by stirring a THF solution of [CpFe(CO)$_2$]$_2$ over a 1% sodium amalgam for 5 h. The anion was then added using a double ended needle to a THF solution of the appropriate alkynyl tosylate cooled to 0° C. The resulting mixture was allowed to warm to 25° C. over 1 h. The solvent was removed by rotary evaporation. The remaining residue was washed with pentane until the washes were colorless. The pentane was removed by rotary evaporation. The crude product was vacuum dried and purified by column chromatography on alumina.

The complex cyclopentadienyl (3-cyclohexenyl-2propynyl)dicarbonyl iron was prepared in 84% yield from 1-Tosyl-3-cyclohexenyl-2-propyne. Likewise, iron alkynyl complexes cyclopentadienyl (3-(4-methoxy)phenyl-2-propynyl)dicarbonyl iron and cyclopentadienyl(3-(4-tert-butyl)phenyl-2-propynyl)dicarbonyl iron may be prepared from tosylates 1-Tosyl-3-(4-methoxy)phenyl-2-propyne and 1-Tosyl-3-(4-tert-butyl)phenyl-2-propyne in 72% and 97% yield respectively.

Cyclopentadienyl(3-cyclohexenyl-2-propynyl)dicarbonyliron.

The iron anion was generated from $[CpFe(CO)_2]_2$ (3.68 g, 10.4 mmol) and was added to a THF solution of 1-Tosyl-3-cyclohexenyl-2-propyne (5.50 g, 18.9 mmol) using the procedure outlined previously. The product was obtained as a brown solid (4.68 g, 15.8 mmol, 83.5%): m.p. 52–53° C. IR (NaCl): 2932, 2002, 1944 $cm^{-1}$. $^1H$ NMR ($C_6D_6$): 6.10 (m, 1 H), 4.08 (s, 5 H), 2.25 (m, 2 H), 1.89 (br s, 4 H), 1.41 (m, 4 H). $^{13}C$ NMR ($C_6D_6$): 216.88, 130.55, 123.22, 98.51, 85.98, 53.61, 30.47, 25.88, 22.88, 22.08, −18.19. Anal. Calcd for $C_{16}H_{16}FeO_2$: C, 64.89; H, 5.45. Found: C, 64.18; H, 5.45.

Cyclopentadienyl(3-(4-methoxy)phenyl-2-propynyl)dicarbonyliron.

The iron anion was generated from $[CpFe(CO)_2]_2$ (3.26 g, 9.23 mmol) and was added to a THF solution of 1-Tosyl-3-(4-methoxy)phenyl-2-propyne (5.31 g, 16.8 mmol) using the procedure outlined previously. The product was obtained as a dark red solid (3.87 g, 12.0 mmol, 71.5%): m.p. 60–61° C. IR (NaCl): 2003, 1949, 1505, 1238, 827 $cm^{-1}$. $^1H$ NMR ($C_6D_6$): 7.45 (d, J=8.0 Hz, 2 H), 6.66 (d, J=8.2 Hz, 2 H), 4.09 (s, 5 H), 3.21 (s, 3 H), 1.95 (s, 2 H). $^{13}C$ NMR ($C_6D_6$): 216–88, 158.93, 132.63, 118.96, 114.30, 99.94, 85.99, 83.65, 54.70, −18.43. Anal. Calcd for $C_{17}H_{14}FeO_3$: C, 63.38; H, 4.38. Found: C, 63.18; H, 4.66.

Cyclopentadienyl(3-(4-tert-butyl)phenyl-2-propynyl)dicarbonyliron.

The iron anion was generated from $[CpFe(CO)_2]_2$ (0.355 g, 1.01 mmol) and was added to a THF solution of 1-Tosyl-3-(4-tert-butyl)phenyl-2-propyne (0.626 g, 1.83 mmol) using the procedure outlined previously. The product was obtained as a dark red solid (0.615 g, 1.77 mmol, 97%): m.p. 58–59° C. IR (NaCl): 2961, 2009, 1951, 825 $cm^{-1}$. $^1H$ NMR ($C_6D_6$): 7.53 (d, J=8.4 Hz, 2 H), 7.16 (d, J=8.4 Hz, 2 H), 4.08 (s, 5 H), 1.93 (s, 2 H), 1.16 (s, 9 H). $^{13}C$ NMR ($C_6D_6$): 216.78, 149.50, 131.11, 125.54, 123.80, 101.06, 85.94, 53.95, 34.52, 31.22, −18.55. Anal. Calcd for $C_{20}H_{20}FeO_2$: C, 68.98; H, 5.79. Found: C, 69.22; H, 5.99.

D. Cycloaddition of Iron Alkynyl Complexes with Sulfur Dioxide

The transition-metal mediated [3+2] cycloadditions of the iron alkynyl complexes with sulfur dioxide were performed as follows: The appropriate iron allenyl or propargyl complex was dissolved in $CH_2Cl_2$ (10–15 mL), purged with nitrogen and cooled to −78° C. Sulfur dioxide (10 mL) was condensed at −78° C. into the iron complex solution. The reaction mixture was allowed to warm to 25° C. under nitrogen to allow evaporation of excess sulfur dioxide. The solvent was removed by rotary evaporation and the remaining solid was vacuum dried.

Alkynyl complex cyclopentadienyl (3-cyclohexenyl-2propynyl)dicarbonyliron cyclized with $SO_2$ to produce the iron sulfenate ester cyclopentadienyl(1-oxo-5-cyclohexenyl-1,2,oxathiol-4-3n-4-yl)dicarbonyliron in 76% yield. Iron complexes Cyclopentadienyl(3-(4-methoxy)phenyl-2-propynyl)dicarbonyliron and Cyclopentadienyl(3-(4-tert-butyl)phenyl-2-propynyl)dicarbonyliron also cyclized with $SO_2$ yielding the iron sulfenate esters cyclopentadienyl(1-oxo-5-(4-methoxy)phenyl-1,2-oxathiol-4-en-4-yl)dicarbonyliron and cyclopentadienyl(1-oxo-5-(4-tert-butyl)phenyl-1,2-oxathiol-4-en-4-yl)dicarbonyliron in 67% and 66% yield respectively.

Cyclopentadienyl(1-oxo-5-cyclohexenyl-1,2.oxathiol-4-en-4-yl)dicarbonyliron (117).

The iron alkynyl complex, Cyclopentadienyl(3-cyclohexenyl-2-propynyl)dicarbonyliron (1.50 g, 5.07 mmol) was treated with $SO_2$ to generate the crude product, which was purified by recrystallization from $CH_2Cl_2$/pentane to yield a yellow solid (1.39 g, 3.86 mmol, 76.4%): m.p. 104–105° C. (dec.). IR (NaCl): 2925, 2107,1966, 1101, 876 $cm^{-1}$. $^1H$ NMR ($CDCl_3$): 5.80 (t, J=1.1 Hz, I H), 5.35 (d, J=14.6 Hz, I H), 5.00 (d, J=14.6 Hz, I H), 4.93 (s, 5 H), 2.16 (m, 4 H), 1.66 (m, 4 H). $^{13}C$ NMR ($CDCl_3$): 213.63, 213.38, 153.11, 148.81, 131.33, 131.07, 92.60, 85.35, 29.82, 25.62, 22.60, 21.63. Anal. Calcd for $C_{16}H_{16}FeO_4S$: C, 53.35; H, 4.48; Found: C, 52.67; H, 4.48. FAB HRMS (m/e): calcd for (MH+)($C_{16}H_{17}O_4FeS$), 361.0197; found 361.0195.

Cyclopentadienyl(1-oxo-5-(4-methoxy)phenyl-1,2-oxathiol-4-en-4-yl)dicarbonyliron (118).

The iron alkynyl complex, Cyclopentadienyl(3-(4-methoxy)phenyl-2-propynyl)dicarbonyliron (1.50 g, 4.66 mmol) was treated with $SO_2$ to generate the crude product, which was purified by recrystallization from $CH_2Cl_2$/pentane to yield a red-brown solid (1.21 g, 3.13 mmol, 67.2%): m.p. 105–106° C. (dec.). IR (NaCl): 2024, 1966, 1494,1242, 1099, 895 $cm^{-1}$. $^1H$ NMR ($CDCl_3$): 7.31 (d, J=8.1 Hz, 2 H), 6.94 (d, J=8.1 Hz, 2 H), 5.51 (d, J=14.7 Hz, 1 H), 5.13 (d, J=14.7 Hz, 1 H), 4.75 (s, 5 H), 3.83 (s, 3 H). $^{13}C$ NMR ($CDCl_3$): 213.50, 213.30, 159.60, 152.89, 150.31, 131.64, 125.84, 114.02, 92.77, 85.50, 55.30. Anal. Calcd for $C_{17}H_{14}FeO_5S$: C, 52–87; H, 3.65. Found: C, 52.69; H, 3.78.

Cyclopentadienyl(1-oxo-5-(4-tert-butyl)phenyl-1,2-oxathiol-4-en-4-yl)dicarbonyliron (119).

The iron alkynyl complex, Cyclopentadienyl(3-(4-tert-butyl)phenyl-2-propynyl)dicarbonyliron (0.615 g, 1.77 mmol) was treated with $SO_2$ to generate the crude product, which was purified by recrystallization from $CH_2Cl_2$/pentane to yield a yellow solid (0.484 g, 1.17 mmol, 66.5%): m.p. 59–60° C. IR (NaCl): 2961, 2023, 1973, 1109, 897 $cm^{-1}$. $^1H$ NMR ($CDCl_3$): 7.42 (d, J=8.3 Hz, 2 H), 7.32 (d, J=8.0 Hz, 2 H), 5.52 (d, J=14.8 Hz, 1 H), 5.14 (d, J=14.8 Hz, 1 H), 4.73 (s, 5 H), 1.33 (s, 9 H). $^{13}C$ NMR ($CDCl_3$): 213.41, 213.29, 152.34, 151.34, 150.59, 130.51, 130.02, 125.47, 92.88, 85.54, 34.70, 31.33. Anal. Calcd for $C_{20}H_{20}FeO_4S$: C, 58.27; H, 4.89. Found: C, 58.54; H, 4.98.

E. Synthesis of Sulfenate Esters

Iron sulfenate ester of step four is then treated to produce the desired end product: a sulfenate ester. One way to achieve such a result includes treating the iron sulfenate ester with perchloric acid to replace the iron-ligand set with a proton. A complicated mixture of products is produced from this reaction, however, none of which resemble the desired product (120). Additionally, when sulfenate ester 117 was treated with Stryker's reagent, known to deliver hydride by Michael addition, no reaction was observed (Mahoney, et al.).

Rather, a surprising and useful way of deriving the disclosed GST-inducing sulfenate esters from the precursor iron sulfenate esters was developed. In a flame dried flask, CuI (3 equiv.) was suspended in freshly distilled THF (5–10 mL) and the solution was thoroughly purged with nitrogen and cooled to −100° C. Methyllithium (1.5 M in $Et_2O$, 6 equiv.) was added slowly. The resulting solution was allowed to stir for 30 min. at −100° C. In another flame dried flask, the appropriate iron complex was dissolved in THF (5–10 mL) and the solution was thoroughly purged with nitrogen and cooled to −100° C. The iron complex solution was added to the cuprate solution using a double ended needle. The reaction mixture was then allowed to stir at −100° C. for 2 h. Sat. $NH_4Cl$ solution (10–20 mL) was then added. The aqueous layer was extracted with diethyl ether (2×15 mL). The organic extracts were combined and dried with MgSO$_4$. The solvent was removed by rotary evaporation and the remaining oil or solid was vacuum dried. The crude product was purified by column chromatography using silica gel at 0° C. with diethyl ether/pentane (1: 1).

4-Methyl-5-(4-methoxy)phenyl-1,2-oxathiol-4-en-1-yl Oxide (121).

Iron complex 118 (0.200 g, 0.518 mmol) was reacted with the cuprate formed from CuI (0.148 g, 0.777 mmol) and methyllithium (1.4 M in Et$_2$O, 1.11 ml, 1.55 mmol) using the above procedure to produce the crude product which was purified to yield an off-white solid (0.027 g, 0. 120 mmol, 23 %): m.p. 74–75° C. IR (NaCl): 1602, 1501, 1246, 1116 cm$^{-1}$. $^1$H NMR (CDCl$_3$): 7.36 (d, J=8.5 Hz, 2 H), 6.94 (d, J=8.5 Hz, 2 H), 5.58 (d, J=15 Hz, 1 H), 5.14 (d, J=15 Hz, 1 H), 3.82 (s, 3 H), 1.97 (s, 3 H). $^{13}$C NMR (CDCl$_3$): 160.08, 143.43, 139.10, 130.20, 120.72, 114.44, 84.68, 55.34, 11.04. Anal. Calcd for C$_{11}$H$_{12}$O$_3$S: C, 58.91; H, 5.39. Found: C, 59.71; H, 5.54. EI HRMS (m/e) calcd for M+(C$_{11}$H$_{12}$O$_3$S) 224.0507, found 224.0516.

From this, a 14% yield of the sulfenate ester 4-methyl-5-(4-methoxy)phenyl-1,2-oxathiol-4-en-1-yl oxide (121) is produced. Alternatively, treatment of the iron complex 118 with 1.5 and 3 equivalents of the standard methyl cuprate generated from copper (I) iodide and methyl lithium produced sulfenate ester 121 in 23% and 22% yields respectively.

Another method of producing a desired GST-inducing sulfenate ester involves treating an iron sulfenate ester, such as compounds 119 and 117, with 3 equivalents of the same methyl cuprate. From this reaction, the sulfenate esters 4-methyl-5-(4-tert-butylphenyl-1,2-oxathiol-4-en-1-yl oxide (122) and 4-methyl-5-cyclohexenyl-1,2-oxathiol-4-en-1-yl oxide (123) were both isolated in 22% yield.

118 R = (4-MeO)phenyl
119 R = (4-t-Bu)phenyl
117 R = cyclohexenyl

121 R = (4-MeO)phenyl
122 R = (4-t-Bu)phenyl
123 R = cyclohexenyl

From these sequential chemical processes, the sulfenate esters produced are surprisingly effective GST, NQ01 and Ferritin H inducers. In particular, the sulfenate esters 4-methyl-5-(4-methoxy)phenyl-1,2-oxathiol-4-en-1-yl oxide and 4-methyl-5-cyclohexenyl-1,2-oxathiol-4-en-1-yl oxide exhibit high levels of inducing activity.

4-Methyl-5-(4-tert-butyl)phenyl-1,2-oxathiol-4-en-1-yl Oxide (122).

Iron complex 119 (0. 100 g, 0.243 mmol) was reacted with the cuprate formed from CuI (0. 139 g, 0.728 mmol) and methyllithium (1.4 M in Et$_2$O, 1.04 ml, 1.46 mmol) using the above procedure to produce the crude product which was purified to yield an off-white solid (0. 013 g, 0.052 mmol, 22.0%): m.p. 73–74° C. IR (NaCl): 2954, 1123, 963, 694 cm$^{-1}$. $^1$H NMR (CDCl$_3$): 7.43 (d, J=8.6 Hz, 2 H), 7.35 (d, J=8.3 Hz, 2 H), 5.60 (d, J=15.0 Hz, 1 H), 5.15 (d, J=15.1 Hz, 1 H), 1.99 (s, 3 H), 1.31 (s, 9 H). $^{13}$C NMR (CDCl$_3$): 152.15, 143.91, 139.62, 128.55, 125.93, 125.61, 84.76, 34.75, 31.19, 11.08. Anal. Calcd for C$_{14}$H$_{18}$O$_2$S: C, 67.17; H, 7.25. Found: C, 66.77; H, 7.25.

4-Methyl-5-cyclohexenyl-1,2-oxathiol4-en-1-yI Oxide (123).

Iron complex 117 (0.100 g, 0.278 mmol) was reacted with the cuprate formed from CuI (0. 159 g, 0.833 mmol) and methyllithium (1.4 M in Et$_2$O, 1.19 ml, 1.67 mmol) using the above procedure to produce the crude product which was purified to yield a colorless oil (0.012 g, 0.061 mmol, 21.8%). IR (NaCl): 2924, 1123, 971, 694 cm$^{-1}$. $^1$H NMR (CDCl$_3$): 5.96 (m, 1 H), 5.46 (d, J=14.9 Hz, 1 H), 4.99 (d, J=14.9 Hz, 1 H), 2.17 (m, 4 H), 1.92 (s, 3 H), 1.65 (m, 4 H). 13C NMR (CDCl$_3$): 146.22, 137.20, 132.23, 127.01, 84.64, 28.55, 25.58, 22.39, 21.51, 11.23. Anal. Calcd for C$_{10}$HO$_2$S: C, 60.58; H, 7.12. Found: C, 60.84; H, 7.27.

EXAMPLE 2

Compounds Demonstrating Metabolic Gene Induction

The compounds have been prepared and structurally characterized as described in Example 1. BNL.CL2 cells were treated with Oltipraz, compound 121 described above, and compound 123 described above. All compounds were applied to the cells at 100 micromolar concentration for 24 hours. Oltipraz induced a 340% increase in GST alpha mRNA levels. Compound 121 induced a 300% increase and compound 123 induced a 430% increase in GST alpha mRNA levels. Most of the induction occurred in the first 24 hours after treatment with these novel compounds but a subsequent time course showed slight additional increases in GST levels 48 and 72h post treatment (See FIG. 1, for data from induction by compound 123). Western blot analysis of the treated cells confirmed that GST alpha (enzyme capable of performing a known GST conjugating reaction) levels were also up in these cells (See FIG. 2). In addition to GST induction, various compounds have also been tested for their ability to induce DT-diaphorase (NQO1), and Ferritin H. The results are shown in Table 2.

The tested compounds and their chemical structures are:

ALH-561

ALH-562

ED-13.4

ED-14.6

DCF070

ALH 490

TABLE 2

| Compound | mRNA Induction | | |
|---|---|---|---|
| | GST α induction | NQO1 induction | Ferritin H induction |
| None | − | − | − |
| Oltipraz | + | + | + |
| t-BHQ | + | + | + |
| ALH-561 | − | − | ± |

TABLE 2-continued

| Compound | mRNA Induction | | |
|---|---|---|---|
| | GST α induction | NQO1 induction | Ferritin H induction |
| ALH-562 | + | + | + |
| ED 13.4 | + | + | + |
| ED 14.6 | + | + | + |
| DCF 070 | + | + | + |
| ALH-490 | + | + | + |

Cells were exposed to compounds at a final concentration of 80 µM for 24 hours. RNA was isolated and analyzed by Northern blotting for the expression of the indicated genes. Control cells were incubated with vehicle alone (0.4% DMSO). Induction indicates levels of mRNA greater than seen in control cells.

Figure 1:
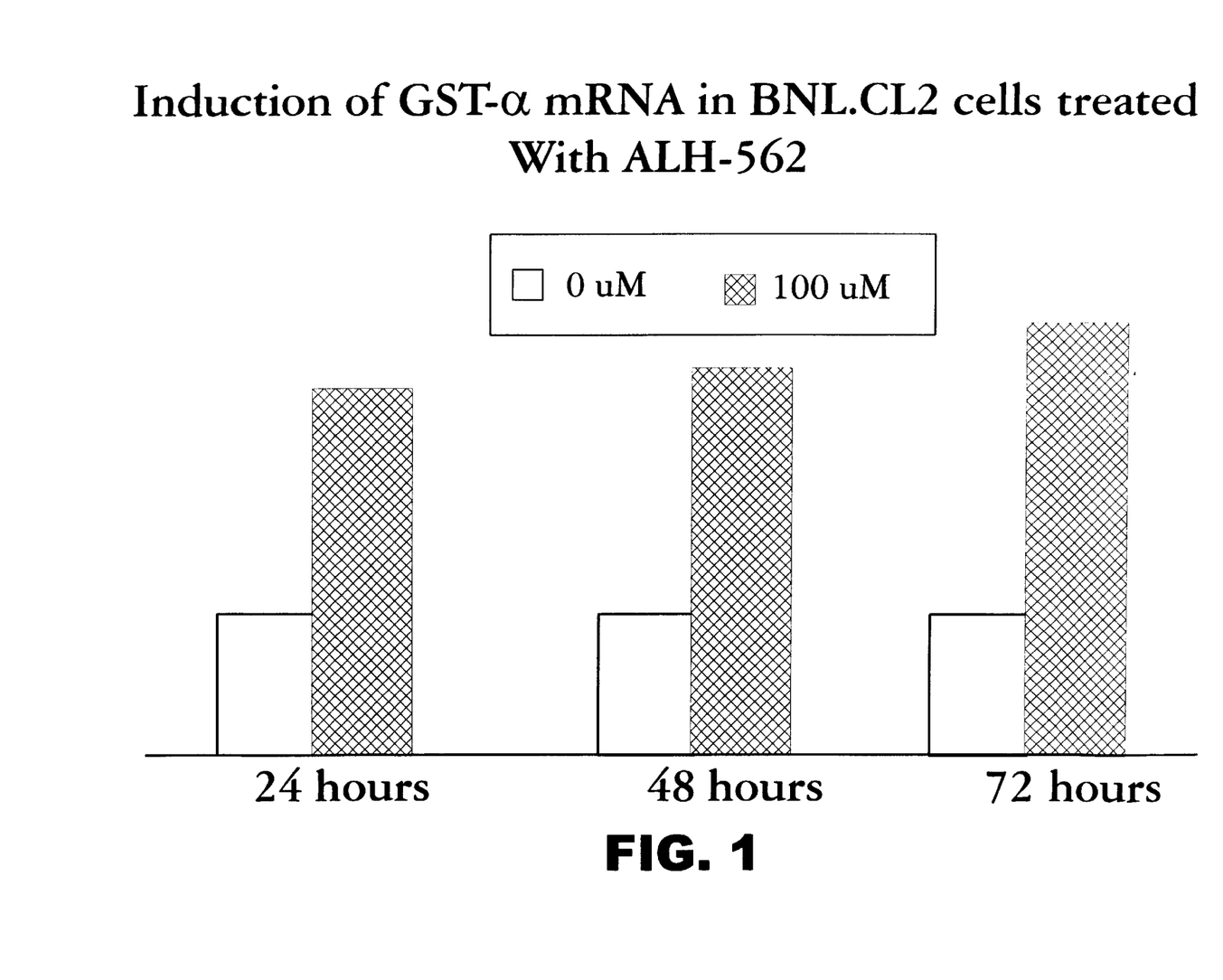
FIG. 1 depicts data showing the induction of GST encoding mRNA in cell culture upon contact with compound 123.
Figure 2:
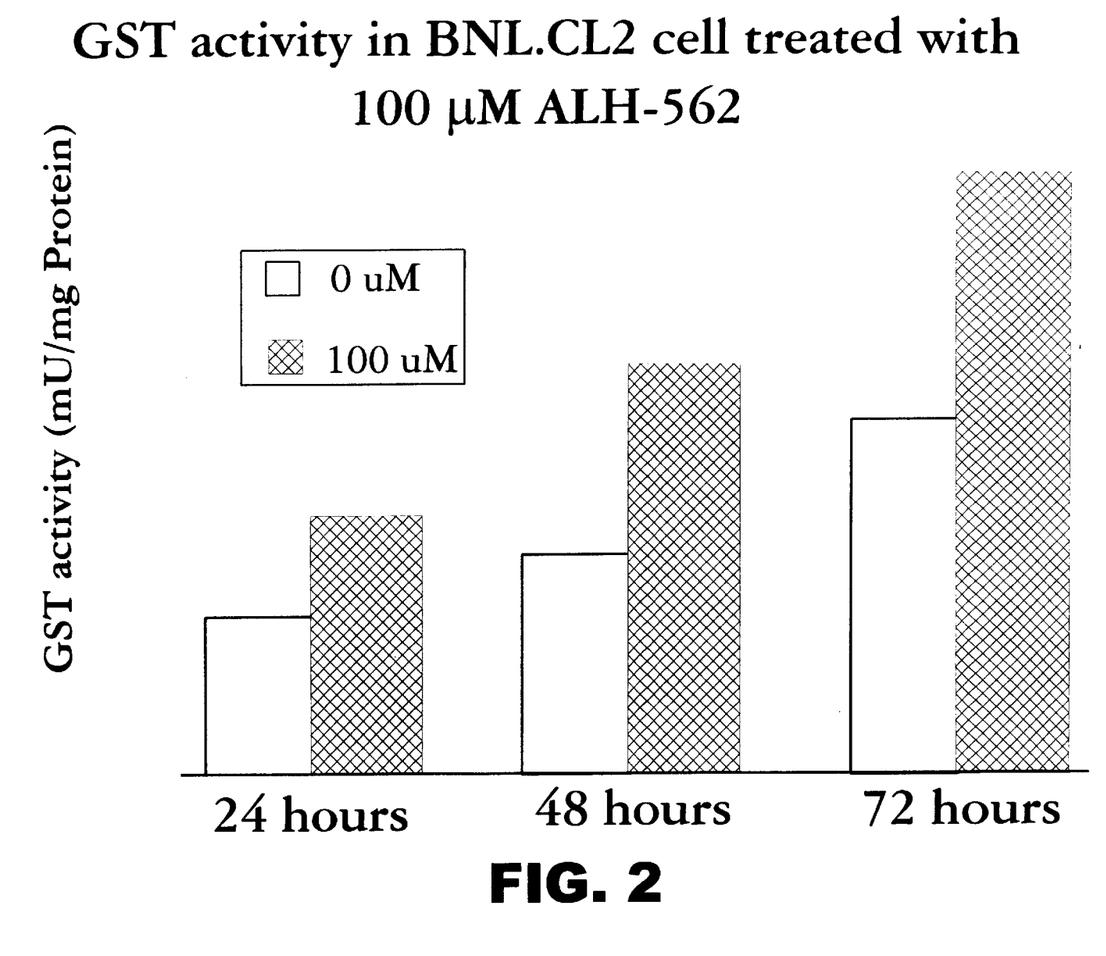
FIG. 2 depicts data showing expression of a GST enzyme in cell culture upon contact with compound 123.

The data described in FIG. 1 was generated using the following techniques.

Northern blot: Treatment of BNL.CL2 cells with 100 µM Oltipraz, ALH-556, and ALH-562, ALH-561, ED 13.4, ED 14.6, DCF 070, ALH-490

BNL.CL2 cells (normal mouse embryonic liver cell line) were plated at ~3×10⁵ cells/ml, grown for 16–24 hours, and treated with 0 µM and 100 µM Oltipraz, ALH-556 (121), and ALH-562 (123) for 24 hours. All three compounds were dissolved in DMSO and the final DMSO concentration present in all treatment conditions was 0.2%. BNL.CL2 cells were harvested by trypsinization and total RNA was isolated using the Trizol reagent (Gibco BRL) according to the manufacturer's procedures. 15 µg of RNA were run on a 1.1% agarose/6.6% formaldehyde gel and transferred overnight onto nitrocellulose membranes by capillary transfer using 20×SSC as transfer buffer. Subsequent to RNA transfer, the nitrocellulose membrane was baked at 80° C. for 2 hours. RNA was analyzed using a radiolabeled mouse ferritin H and human GST-α c-DNA. A human β-actin probe was used as an internal standard. The c-DNA probes were labeled with [α$^{32}$P]dCTP by a random prime labeling. Hybridization of the c-DNA probes to the nitrocellulose membrane was performed at 68° C. for 60 minutes using the Quick-Hyb solution (Stratagene). Membranes were subjected to phosphoimager analysis after hybridization.

Treatment of BNL.Cl2 cells with 100 µM ALH-562 for GST activity measurements and western blot analysis BNL.CL2 cells were set up at ~1×10⁵ cell/ml, grown for 16–24 hours, and treated with 0 µM and 100 µM ALH-562. ALH-562 was dissolved in DMSO and the final concentration of DMSO present in all treatment conditions was 0.2%. After 24, 48, and 72 hours of treatment cells were harvested by scraping into ice cold 1×PBS. Cells were pelleted at 1000 rpm for 5 minutes at 4° C. The pellets were frozen at −20° C. until analysis.

Cell Preparation for GST Assays

At the time of analysis, the pellet was resuspended in 1 volume of 50 mM Tris/5 mM EDTA pH 7.4 and sonicated for 10–15sec. Sample was transferred to a microfuge tube and centrifuiged 13K for 10 min at 4° C. The cytosolic supenate was used in the assays. Proteins were determined by the method of Lowry.

GST Assay

The method used is described in Clapper et al., 1993 and Fields, et al., 1994 and is a modification of the method of Habig et al., 1974. Briefly, 1–50 ul of sample was assayed at 23° C. in a solution of 0.1M potassium phosphate, pH 6.5 and 1 mM GSH (glutathione).

The reaction was initiated with 1 mM (final) 1-chloro 2,4 dinitrobenzene (CDNB) in 20×ethanolic solution. Change in aborbance was monitored at 340 nm for 90 sec. Activity was calculated using the ΔA/min and extinction coefficient, reported in nmol/min/mg protein.

GST Western Blot Assay

Cells were prepared as above. Cytosolic protein samples were boiled in Laemmli buffer for 5 min prior to loading. Samples were electrophoresed on a 12% SDS-PAGE gel and transferred by semidry electroblotting onto nitrocellulose membrane. The blot was blocked with 5% nonfat dry milk in PBS then probed with a 1:1000 dilution of affinity purified rabbit polyclonal anti-human GST in 5% nonfat dry milk. The primary antibodies were produced and purified as described below. The probed blot was washed 4 times in PBS, then incubated with a 1:3000 dilution of goat anti-rabbit HRP-conjugated IgG (Cappel/ICN, Costa Mesa, Calif.). The blot was washed again in PBS and quantitated by chemiluminescence using X-ray film capture.

The purified antibody was prepared by coupling 25 mg of purified human GST (alpha, mu or pi) in 5 ml 0.1M HEPES buffer, pH 7.0, to ethanol washed Affigel-15 (Bio-Rad Hercules, Calif.), followed by blocking of unreacted groups with 1M ethanolamine. Rabbit antisera developed against hGST alpha, mu or pi and containing 10 mM $KPO_4$, 0.4M NaCl and 10 mM EDTA pH 7.4 was passed over the column followed by washing with several column volumes of the same buffer containing 1M NaCl. Purified polyclonal antisera monospecific for either hGST alpha, pi or mu was eluted with 0.1M glycine, pH 2.8, 1M NaCl, neutralized and dialyzed against 10 mM $KPO_4$, pH 7.4 and 50% glycerol.

EXAMPLE 3

Compositions Demonstrating anti-HIV Activity

In earlier studies, the present inventor has investigated the reactions and interactions of $S_2O$ and $SO_2$ with a variety of transition-metal complexes and has developed some new routes to sulfur heterocycle synthesis based on this transition-metal chemistry (Welker, 1992). In these studies of new transition-metal sulfur chemistry, the aim was to be able to (i) generate $S_2O$ cleanly; (ii) synthesize transition-metal $S_2O$ complexes and investigate their reaction chemistry, and (iii) investigate 3+2 cycloaddition reactions Of $S_2O$ and $SO_2$ with transition-metal propargyl, allenyl and allyl complexes.

Synthesis of an $S_2O$ Precursor Molecule.

All of the proposed transition-metal $S_2O$ chemistry depended on the ready availability of an $S_2O$ source. Prior to this work, $S_2O$ was typically produced by pyrolysis methods which produced other sulfur oxides in addition to $S_2O$ (Dodson et al., 1972; Murthy et al., 1971). The present inventor developed a simple synthesis of 4,5-diphenyl-1,2-dithiin-1-oxide (12) which liberated $SO_2$ via a retro Diels-Alder reaction (Fulcher et al., 1993; Urove et al., 1990; Urove and Welker, 1988). Compound 12 was chosen as a potential $S_2O$ precursor because it was contemplated that the steric interaction between the two phenyls in 12 would accelerate the retro Diels-Alder reaction and the resulting diene (13) should exist almost exclusively in the s-trans conformation at relatively low temperatures, thereby inhibiting Diels-Alder reactions with the $S_2O$ once it was liberated.

3+2 Cycloaddition Reactions.

The preferred synthetic methodology has been in the area of transition-metal-mediated 3+2 cycloaddition reactions. Transition-metal propargyl complexes react cleanly with 12 in THF at 25° C. to produce metallothiosulfinate esters (17) (Raseta et al., 1991; Raseta et al., 1989). The rates of these cycloadditions increased as the nucleophilicity of the metal propargyls (15) increased. Surprisingly these reactions also proceeded at 25° C. and a transition-metal nucleophile induced electrocyclic ring opening of 12 was proposed to account for the observed products. This mechanism is consistent with MNDO predictions of the structure of 12 (12 is predicted to have a very weak C—S bond between the $CH_2$ and oxidized sulfur)(Urove et al., 1990). The crystal structure of one of these metallothiosulfinate esters (17)($L_nM$= $CpFe(CO)_2$, R=Ph) was also solved to rigorously prove the presence of the S—S=O rather than O—S=S linkage in the heterocycle (Raseta et al., 1991).

The metals were removed from complexes (18) via oxidative carboxylation to produce carboethoxy substituted five-membered-ring thiosulfinate esters ($S_2O$)(Raseta et al., 1991; Raseta et al., 1989; Stokes et al., 1995; Ni et al., 1992).

Recently in the metal propargyl/allenyl cyclization area, studies of 3+2 cycloadditions of allenyl complexes (23, 26) with SO$_2$ have shown that these cyclizations produce regioisomers (25, 28) of the propargyl cyclization products (22) (Hurley et al., 1998). The structure of the cyclization product (25a) from the simplest allene was confirmed by X-ray crystallography (Hurley et al., 1998). Complex 25b was produced as a 2.3:1 mixture of diastereomers. The major diastereomer (25b anti) had the anti orientation of the oxygen and methyl groups as proven by shift reagent studies (Hurley et al., 1998). Iron allenyl complex cycloaddition chemistry has not been studied to the extent propargyl chemistry has (Thomasson et al., 1971; Rosenblum and Watkins, 1990). These cyclization reactions presumably proceed via intermediates (24 & 27) analogous to the one (21) reported for the propargyl cyclizations (Thomasson et al., 1971).

Oxidative carboxylation was used to produce new sulfenate esters (29) and cuprates generated from MeLi or MeMgBr were used to produce the demetallated cyclic sulfenate ester (30).

It is contemplated that saturated five membered ring sulfur heterocycles may also be produced using this organometallic methodology (Hayes and Welker, 1998). However, the unsaturated sulfur heterocyclic iron complexes appear to be much more stable than the saturated ones so the present example focuses on the preparation of the unsaturated heterocycles.

Biological Screening.

Nine five membered ring thiosulfinate esters and sulfenate esters (53a–h) screened show significant cytoprotection in the XTT assay (Table 3) and two of these compounds (53a and f) have EC$_{50}$'s below that of the best dithiane (8, NSC 624151) described above. Based on these preliminary screens, it is contemplated that an aromatic or large substituent at R$_1$ (compare entries 1 & 4, 9 & 10) and a small substituent at R$_2$ (compare entries 1, 2, & 3; 7, 8, & 9) may be best for anti-HIV-1 activity. Sulfur heterocycles containing more than 6 atoms don't appear to be active (entries 13 & 14). In the one case where the sulfur oxidation state was examined here (entries 11 & 12) sulfur oxidation did prove to be important for zinc ejection as noted earlier for 6, 7, 8 & 9 (Rice et al., 1997). As observed for 8 previously (Rice et al., 1997), anti-HIV-1 activity and toxicity of 53a went down when treated with 2 equivalents of GSH (entry 6). However unlike 8, zinc ejecting ability of 53a was little effected by GSH. The XTT cytoprotection assay data for 53a and 53f are almost identical and thus this data is reported (FIG. 1) for 53f as a representative example only.

(53a–g, Welker 5-ring Compounds)(7, NSC 661126)(8, NSC 624151)(53h, Welker Large Ring Compound)

TABLE 3

Antiviral Activity and NCp7 Zn ringer reactivity of rive member ring sulfur heterocycles.

| Compound | X | $R_1$ | $R_2$ | XTT Anti-HIV-1 Assay $EC_{50}$ (µM) | $IC_{50}$ (µM) | NCp7 Trp37 Assay (% Decrease RFU/ 30 min) 50 µM without GSH | 50 µM with GSH |
|---|---|---|---|---|---|---|---|
| (1) 53a | S | Ph | $CO_2Me$ | 6 | 18 | 13.5 | |
| (2) 53b | S | Ph | $CO_2Et$ | a | 45.7 | 6.5 | |
| (3) 53c | S | Ph | $CO_2iPr$ | b | 15.2 | 17.1 | |
| (4) 53d | S | Me | $CO_2Me$ | c | 16.9 | 14.3 | |
| (5) 53e | S | Me | $CO_2iPr$ | d | 18.4 | 10.4 | |
| (6) 53a + GSH | S | Ph | $CO_2Me$ | *17.3 | | | 16.7 |
| (7) 53f | O | Ph | Me | 5.9 | 16.9 | 0 | |
| (8) 53g | O | Ph | $CO_2Et$ | e | 213 | 26 | |
| (9) 53h | O | Ph | $CO_2Me$ | f | 22.5 | 0 | |
| (10) 53g | O | Me | $CO_2Me$ | g 5.3 | | 0.2 | |
| NSC661126 (7) | | | | 9.8 | 30 | 18 | |
| NSC624151 (8) | | | | 6.6 | 184 | 17 | |
| NSC624151 /GSH | | | | 64.2 | >200 | | |

[a] Maximum cytoprotection 31.6% @ 10 µM. [b] Maximum 43.3% cytoprotection @ 10 µM.
[c] Maximum 41.4% cytoprotection @ 10 µM. [d] Maximum 40% cytoprotection @ 10 µM. [e] Maximum 12% cytoprotection @ 100 µM. [f] Maximum cytoprotection 29% @ 10 µM. [g] Maximum 32.6% cytoprotection @ 3.2 µM. [h] Maximum 31% cytoprotection @ 31.6 µM. * Maximum 44% cytoprotection at 95 µM.

Thus, the disclosed compounds, prepared by a novel method, and including the newly disclosed compound 53a, as well as compound 53f, for example, are demonstrated to possess anti-HIV-1 activity.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the methods described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Armstrong, Chem. Res. Toxicol., 1991, 4, 131.
Baudouy et al., Tetrahedron, 1980, 36, 189.
Bondarenko, et al., Russian Chem. Rev., 1996, 64, 147.
Brandsma and Verkruijsse, Synthesis of Acetylenes, Allenes, and Cumulenes; Elsevier Publishing Co., New York, 1981, p. 65.
Bransdma, Preparative Acetylenic Chemistry; Elsevier Publishing Co.: New York, 1971, 267.
Braverman and Duar, J. Am. Chem. Soc., 1983, 105, 1061.
Bunting, K. D, Lindahl, R. and Townsend, A J. (1994) Oxazaphosphorine-specific resistance in human MCF-7 breast carcinoma cell lines expressing transfected rat class 3 aldehyde dehydrogenase. J. Biol Chem 269 (37), pp. 23197–23206.
Clapper, M. L, Everley, L. C. Strobel, L. A, Townsend, A. J. and Engstrom P. F. (1993) Coordinate induction of glutathione S-transferase α, µ, and π expression in murine liver after a single administration of oltipraz. Mol Pharm 45, pp. 469–474.
Dimitrov et al., "clinical Pharmacology Studies of Oltipraz—A Potential Chemopreventive Agent," Invest. New Drugs, 10:289–98, 1992
Dieter, et al., Tetrahedron Lett., 1997, 38, 783.
Emester, L. (1967) DT diaphorase. Meth Enzymol 10 pp. 309–317.
Ernester, L. (1987) DT diaphorase, a historical review. Chem Scripta 27A pp. 1–13.
Fields, W. R., Li, Ying, and Townsend, A J. Protection by Transfected Glutathione S-Transferase Isoenzymes Against Carcinogen-Induced Alkylation of Cellular Macromolecules in Human MCF-7 Cells. Carcinogenesis, 15: 1155–1160, 1994.
Foxman et al., J. Am. Chem. Soc., 1977, 99, 2160.
Habig, W., Pabst, M. and Jakoby, W. (1974) Glutathione s-transferase: the first enzymatic step in mercapturic acid formation J. Biol. Chem. 249, pp. 7130–7139.
Harding, D. , Jackson, M. R., Wooster, R., Foumel-Gigleux, S., and Burchell, B. (1988) Cloning and substrate specificity of an human phenol UDP-glucuronosyltransferase expressed in COS-7 cells. Proc Natl Acad Sci USA 85 pp. 8381–8385.
Harpp et al., J. Org. Chem., 1976, 41, 3987.
Harris et al., J. Chem. Soc. Perk. Trans. I, 1976, 1612.
Jolly and Pettit, J. Organometallic Chem., 1968, 12, 491.
Jung et al., J. Am. Chem. Soc., 1973, 95, 3420.
Kato and Numata, Tetrahedron Lett., 1972, 203.
Kensler et al., Chem. Res. Toxicol. 1999, 12, 113.

Kensler et al., In Food *Phytochemicals for Cancer Research*, Huang et al., eds.: American Chemical Soc. 1994, 154.
Kessler, F. K. and Ritter J. K. (1997) Induction of a rat liver benzo[a]pyrene-trans-7,8-dihydrodiol glucuronidating activity by oltipraz and β-naphthoflavone. Carcinogenesis 18 (1) pp. 107–114.
King, et al., *Can. J. Chem.*, 1970, 48, 3704.
Kondo et al., *J. Org. Chem.*, 1997, 62, 6507
Legler et al.,*Tetrahedron Lett.*, 1972, 3907.
Liskamp et al., *J. Org. Chem.*, 1981, 46, 5408.
Lowry, O. H., Rosenbrough, N. J., Farr, A. L., and Randall, R. J. (1951) Protein measurement with the Folin agents. J. Biol Chem 193 pp. 265–275.
Mahoney et al., *J. Am. Chem. Soc.*, 1988, 110, 291
Marszak-Fleury, *Ann. Chim. Paris* 1958, Ser. 13, 3, 657.
Miyaura, et al., *Chemistry Letters*, 1979, 535.
Nemoto, N. and Gelbion, H. V. (1976) Enzymatic conjugation of benzo[a]pyrene oxides, phenols and dihydrodiols with UDP-glucuronic acid. Biocem Pharm 25 pp. 1221–1226.
Olah and Kuhn, *J. Am. Chem. Soc.*, 1962, 84, 3684.
Owens, I. S. (1977) Genetic regulation of UDP-glucuronosyltransferase induction by polycyclic aromatic compounds in mice. J. Biol Chem. 252 (9) pp. 2827–2833.
Piper et al., *J. Inorg. & Nuc. Chem.*, 1955, 1, 165.
Ritter, J. K., Crawford, J. M., and Owens, I. S. (1991) Cloning of two human liver bilirubin UDPglucuronosyltransferase cDNAs with expression in COS-1 cells. J. Biol Chem 266 pp. 1043–1047.
Roustan and Cadiot, *Acad. Sci.*, 1969, 268, 734.
Ryter, S., Kvam, E., Richman, L, Hartmann, F., and Tyrrell, R. M. (1998) A chromatographic assay for heme oxygenase activity in cultured human cells: Application to artificial heme oxygenase overexpression.
Singh and Lippman, "Cancer Chemoprevention Part I: Retinoids and Carotenoids and other classic antioxidants," *Oncology*, 12:1643–58, 1998.
Squires et al., *J. Org. Chem.*, 46, 2373, 1981.
Summers, *Protein, Sci.*, 1, 563, 1992.
Talalay, et al., *Proc. Natl. Acad. Sci. USA*, 85, 8261, 1988.
Talalay, "Mechanism of induction of enzymes that protect against carcinogenesis," *Adv. Enz. Reg.* 28:237–50, 1989
Thoumazeau et al, *Heterocycles*, 19, 2247, 1982.
Vienneau, et al. "Potential genoprotective role for UDPglucuronosyltransferases in chemical carcinogenesis: Initiation of micronuclei by benzo(a)pyrene in UDP-glucuronosyltransferase-deficient cultured rat skin fibroblasts," *Cancer Res* 55:1045–51, 1995.
Vreman and Stevenson "Heme oxygenase activity as measured by carbon monoxide production," *Anal. Biochem* 168:31–38, 1988.
Wadsworth et al., *J. Org. Chem.*, 52, 3662, 1987.
Wattenberg, "An overview of chemoprevention: current status and future prospects," *Proc. Soc. Exp. Biol. Med.*, 216:133–41, 1997.
Wawerski and Basolo, *Inorg. Chem. Acta*, 3, 113, 1969.
Weislow et al., *J. Nat. Cancer Inst.*, 81, 577, 1989.
Whelan, et al. "Differential increased glutathione S-transferase activities in a range of multidrug-resistant human cell lines," *Cancer Communications* 1:359–65, 1989
Yanagawa et al., *Tetrahedron Lett.*, 1973, 1073
Yang and Burton, *Tetrahedron*, 1990, 31, 1369.

What is claimed is:

1. A composition comprising a five membered ring thiosulfinate ester, or a five-membered ring sulfenate ester, wherein the five membered ring has structure (1)

(I)

wherein, X is O or S;

$R_1$ is an alkyl with from 1 to 6 carbon atoms, pheryl, substituted phenyl, cyclohexenyl, or substituted cyclohexenyl, $R_2$ is alkyl, phenyl or $CO_2R_3$, wherein $R_3$ is alkyl or phenyl; and when X is O and $R_1$ is phenyl, $R_2$ is not alkyl or phenyl and $R_3$ is not alkyl;

when X is O and $R_1$ is methyl, $R_2$ is not phenyl and $R_3$ is not methyl; and when X is S and $R_2$ is $CO_2Et$, $R_1$ is not methyl, phenyl or isoprenyl.

2. The composition of claim 1, wherein when $R_1$ is a substituted phenyl, said substituted phenyl is substituted at the 4 position with a methoxy, t-butyl, alkyl ketone, sulfonamide, or trifluoromethyl group.

3. The composition of claim 1, wherein when $R_1$ is a substituted cyclohexenyl, said cyclohexenyl is substituted in the 2 position with a halogen, an alkyl, or a phenyl.

4. The composition of claim 1, wherein X is O, $R_1$ is (4-MeO)phenyl, (4-t-Bu)phenyl or cyclohexenyl and $R_2$ is methyl.

5. The composition of claim 4, wherein $R_1$ is (4-MeO) phenyl.

6. The composition of claim 4, wherein $R_1$ is (4-t-Bu) phenyl.

7. The composition of claim 4, wherein $R_1$ is cyclohexenyl.

8. The composition of claim 1, wherein X is O, $R_1$ is cyclohexenyl, and $R_2$ is alkyl or phenyl.

9. The composition of claim 8, wherein $R_2$ is methyl.

10. The composition of claim 1, wherein X is O, $R_1$ is (4-MeO)phenyl and $R_2$ is $CO_2R_3$.

11. The composition of claim 1, wherein X is O, and $R_1$ is (4-trifluoromethyl)phenyl.

12. The composition of claim 1, wherein X is O, and $R_1$ is phenyl (4-alkyl ketone).

13. The composition of claim 1, wherein X is O, and $R_1$ is phenyl (4- sulfonamide).

14. The composition of claim 1, wherein X is O, and $R_1$ is a cyclohexenyl with a halogen substitution at the 2 position.

15. The composition of claim 14, wherein said halogen is chloride, fluoride, bromide or iodide.

16. The composition of claim 1, wherein X is O, $R_1$ is a cyclohexenyl with an alkyl substitution at the 2 position.

17. The composition of claim 16, wherein said alkyl is an alkyl comprising 1 to 6 carbon atoms.

18. The composition of claim 1, wherein X is O, and $R_1$ is a cyclohexenyl with a phenyl substitution at the 2 position.

19. The composition of claim 1, wherein X is S, $R_1$ is phenyl or methyl, $R_2$ is $CO_2R_3$ and $R_3$ is phenyl.

20. The composition of claim 19, wherein $R_1$ is phenyl.

21. The composition of claim 19, wherein $R_1$ is methyl.

22. The composition of claim 1, wherein X is S, $R_1$ is (4-MeO)phenyl, (4-t-Bu)phenyl or cyclohexenyl and $R_2$ is methyl.

23. The composition of claim 22, wherein $R_1$ is (4-MeO)phenyl.

24. The composition of claim 22, wherein $R_1$ is (4-t-Bu)phenyl.

25. The composition of claim 22, wherein $R_1$ is cyclohexenyl.

26. The composition of claim 1, wherein X is S, $R_1$ is phenyl, and $R_2$ is alkyl.

27. The composition of claim 26, wherein $R_2$ is methyl, ethyl, propyl, or isopropyl.

28. The composition of claim 1, wherein X is S, $R_1$ is cyclohexenyl, and $R_2$ is alkyl or phenyl.

29. The composition of claim 28, wherein $R_2$ is methyl.

30. The composition of claim 1, wherein X is S, $R_1$ is (4-MeO)phenyl and $R_2$ is $CO_2R_3$.

31. The composition of claim 1, wherein X is S, and $R_1$ is (4-trifluoromethyl)phenyl.

32. The composition of claim 1, wherein X is S, and $R_1$ is phenyl (4-alkyl ketone).

33. The composition of claim 1, wherein X is S, and $R_1$ is phenyl (4-sulfonamide).

34. The composition of claim 1, wherein X is S, and $R_1$ is a cyclohexenyl with a halogen substitution at the 2 position.

35. The composition of claim 34, wherein said halogen is chloride, fluoride, bromide or iodide.

36. The composition of claim 1, wherein X is S, $R_1$ is a cyclohexenyl with an alkyl substitution at the 2 position.

37. The composition of claim 36, wherein said alkyl is an alkyl comprising 1 to 6 carbon atoms.

38. The composition of claim 1, wherein X is S, and $R_1$ is a cyclohexenyl with a phenyl substitution at the 2 position.

39. A composition of claim 1, wherein the ring comprises an additional element Y as shown in structure (II):

(II)

40. The composition of claim 39, wherein Y is O.

41. The composition of claim 40, wherein $R_1$ is phenyl and $R_2$ is methyl or phenyl.

42. A preparation comprising a composition of claim 1 contained in a pharmaceutically acceptable carrier.

43. A preparation of claim 42, wherein said preparation is formulated for oral administration.

44. A pharmaceutical composition effective to inhibit an incidence of cancer in a subject when administered to said subject, said composition comprising a five membered ring thiosulfinate ester, or a five-membered ring sulfenate ester, wherein the five membered ring has structure (II);

(II)

and further wherein when X is O or S;
$R_1$ is methyl, phenyl, substituted phenyl, cyclohexenyl, or substituted cyclohexenyl;
$R_2$ is methyl, phenyl, hydrogen or $CO_2R_3$, wherein $R_3$ is alkyl or phenyl; and Y is not present or Y is O.

45. The pharmaceutical composition of claim 44, wherein said pharmaceutical composition is further defined as comprising a unit dose effective to induce expression of a Phase II response enzyme in said subject when said composition is administered to said subject on a onetime or periodic basis.

46. The pharmaceutical composition of claim 45 wherein said Phase II response enzyme is glutathione-S-transferase (GST), DT-diaphorase (NQO1), or Ferritin H.

47. The pharmaceutical composition of claim 44, wherein said subject is an unaffected (normal) individual.

48. The pharmaceutical composition of claim 44, wherein said subject has been exposed to, or is susceptible to being exposed to a carcinogenic xenobiotic agent.

49. The pharmaceutical composition of claim 44, wherein said subject is a human subject.

50. The pharmaceutical composition of claim 44, wherein said pharmaceutical composition is formulated to be administered in an amount of from about 1 to about 1000 mg per unit dose.

51. The pharmaceutical composition of claim 44, wherein said pharmaceutical composition is formulated to be administered in an amount of from about 5 to about 600 mg per unit dose.

52. The pharmaceutical composition of claim 44, wherein said pharmaceutical composition is formulated to be administered in an amount of from about 100 to about 500 mg per unit dose.

53. A pharmaceutical composition effective to inhibit HIV replication in a subject when said composition is administered to said subject, said composition comprising a five membered ring thiosulfinate ester, or a five-membered ring sulfenate ester, wherein the five membered ring has structure (II);

(II)

and further wherein when. X is O or S;
$R_1$ is methyl, phenyl, substituted phenyl, cyclohexenyl, or substituted cyclohexenyl;
$R_2$ is methyl, phenyl, hydrogen or $CO_2R_3$, wherein $R_3$ is alkyl or phenyl; and Y is not present or Y is O.

54. The pharmaceutical composition of claim 53, fisher defined as a pharmaceutical package comprising a unit dose effective to inhibit HIV replication when said composition is administered to a subject periodically.

55. The pharmaceutical composition of claim 53, wherein said subject is a human HIV patient.

56. The pharmaceutical composition of claim 53, wherein said pharmaceutical composition is formulated to be administered in an amount of from about 1 to about 1000 mg per unit dose.

57. The pharmaceutical composition of claim 53, wherein said pharmaceutical composition is formulated to be administered in an amount of from about 5 to about 600 mg per unit dose.

58. The pharmaceutical composition of claim 53, wherein said pharmaceutical composition is formulated to be administered in an amount of from about 100 to about 500 mg per unit dose.

* * * * *

UNITED STATES PATENT AND TRADEMARK OFFICE
CERTIFICATE OF CORRECTION

PATENT NO.    : 6,242,478 B1
DATED         : June 5, 2001
INVENTOR(S)   : Welker et al.

It is certified that error appears in the above-identified patent and that said Letters Patent is hereby corrected as shown below:

Claim 1,
Line 3, delete the numeral "(1)" and insert therefor -- (I) --.
Line 5, delete the word "pheryl" and insert therefor -- phenyl --.

Claim 53,
Line 7, delete the punctuation mark "." immediately following the word "when".

Claim 54,
Line 1, "fisher" and insert therefor -- further --.

Signed and Sealed this

Twenty-ninth Day of January, 2002

Attest:

Attesting Officer

JAMES E. ROGAN
*Director of the United States Patent and Trademark Office*